United States Patent [19]

Greenhut et al.

[11] Patent Number: 5,591,215

[45] Date of Patent: *Jan. 7, 1997

[54] APPARATUS AND METHOD FOR DETECTION OF ATRIAL FIBRILLATION BY VENTRICULAR STABILITY AND VENTRICULAR PACING

[75] Inventors: Saul E. Greenhut, Aurora, Colo.; Anthony Murphy, Annandale, Australia

[73] Assignee: Telectronics Pacing Systems, Inc., Englewood, Colo.

[*] Notice: The term of this patent shall not extend beyond the expiration date of Pat. No. 5,480,413.

[21] Appl. No.: 560,447

[22] Filed: Nov. 17, 1995

Related U.S. Application Data

[63] Continuation-in-part of Ser. No. 347,279, Nov. 30, 1994, Pat. No. 5,480,413.

[51] Int. Cl.$^6$ .................... A61N 1/365; A61B 5/0452
[52] U.S. Cl. .................... 607/14; 607/4; 128/705
[58] Field of Search .................... 607/4, 9, 14, 25; 128/702, 705

[56] References Cited

U.S. PATENT DOCUMENTS

| | | | |
|---|---|---|---|
| 4,998,974 | 3/1991 | Aker . | |
| 5,193,536 | 3/1993 | Mehra | 607/4 |
| 5,282,836 | 2/1994 | Kreyenhagen et al. | 607/4 |
| 5,356,425 | 10/1994 | Bardy et al. | 607/14 |
| 5,411,524 | 5/1995 | Rahul | 607/4 |
| 5,480,413 | 1/1996 | Greenhut et al. | 607/14 |

FOREIGN PATENT DOCUMENTS

WO9323115  11/1993  WIPO .

OTHER PUBLICATIONS

A Quantitative Model for the Ventricular Response During Atrial Fibrillation, Richard J. Cohen, Ronald D. Berger, Theodore E. Dushane, IEEE Transactions on Biomedical Engineering, vol. BME-30, No. 12, pp. 769–781, Dec., 1983.

Rate Stabilization by Right Ventricular Pacing in Patients with Atrial Fibrillation, F.H.M. Wittkampf and M.J.L. DeJongste, PACE, vol. 9, pp. 1147–1153.

Effect of Right Ventricular Pacing on Ventricular Rhythm During Atrial Fibrillation, F.H.M. Wittkampf, Mike J.L. deJongste, Henk I. Lie, Frits L. Meijler, ACC vol. 11 No. 3, pp. 539–545, Mar., 1988.

A New Pacing Method for Rapid Regularization and Rate Control in Atrial Fibrillation, Chu–Pak Lau, Wing–Hung Leung, Cheuk–Kit Wong, Yau–Ting Tai and Chun–Ho Cheng, The American Journal of Cardiology, vol. 65, pp. 1198–1203, May 15, 1990.

*Primary Examiner*—William E. Kamm
*Assistant Examiner*—George R. Evanisko
*Attorney, Agent, or Firm*—Gottlieb, Rackman & Reisman

[57] ABSTRACT

A cardiac implant device is provided in which the ventricular rate is monitored to differentiate between atrial fibrillation and ventricular tachycardia or other cardiac conditions. For this purpose, the ventricular rate stability is monitored by, for example, measuring the R-R intervals of successive ventricular beats. If the ventricular rate is found to be unstable, the ventricle is paced at a test rate to try to stabilize the ventricle. If the attempt is unsuccessful, atrial fibrillation is assumed and, if necessary, corresponding therapy is applied. If the attempt is unsuccessful, atrial fibrillation is eliminated as a cause of the ventricular rate instability and other types of classifying and treating the cardiac condition may be used.

19 Claims, 5 Drawing Sheets

APPARATUS AND METHOD FOR DETECTION OF ATRIAL FIBRILLATION BY VENTRICULAR STABILITY AND VENTRICULAR PACING

RELATED APPLICATIONS

This is a continuation-in-part to application Ser. No. 347,279, filed Nov. 30, 1994, entitled APPARATUS AND METHOD FOR STABILIZING THE VENTRICULAR RATE OF A HEART DURING ATRIAL FIBRILLATION, now U.S. Pat. No. 5,480,413.

BACKGROUND OF THE INVENTION

A. Field of Invention

In the following description, the term 'pacemaker' is used generically to cover implantable antitachycardia devices as well as permanent, temporary and/or external pacemakers and implantable cardioverter defibrillators (ICD's) used to detect cardiac arrhythmia and fibrillation and, optionally, to provide appropriate therapy, if required. The subject invention pertains to pacemakers, and more particularly to a pacemaker with means for discriminating atrial fibrillation from ventricular tachycardia and/or other supraventricular tachycardia through a novel technique by monitoring ventricular rate stability.

B. Description of the Invention

Patients with pacemakers may experience cardiac arrhythmia which may be due (among other causes) to atrial fibrillation or ventricular tachycardia. Atrial fibrillation (AF), while uncomfortable and having deleterious long term effects does not constitute an immediate danger, by itself, to the patient and accordingly, the normal clinical approach to such a condition is to ignore it or to treat it in what is, in many cases, an inadequate manner. For example, AF is often treated by administration of various drugs. However, these drugs have side effects, may not control ventricular rate satisfactorily and typically prevent the recurrence of AF for only a limited time.

One indirect result of atrial fibrillation in patients with intact AV nodal conduction may be a relatively high and irregular ventricular rate. In other words, during atrial fibrillation, the ventricular intervals may vary substantially from one ventricular event to the next. The mechanism for this biological phenomenon is not understood completely. It has been suggested that, during atrial fibrillation, the AV node receives numerous successive stimuli originating from the atrium, and while each stimulus alone has a low amplitude which is insufficient to trigger a ventricular contraction, they do cause partial depolarizations. The effects of these partial depolarizations is cumulative, so that when a sufficient number of such stimuli are received, the AV node is depolarized resulting in unstable random ventricular contractions. (See R.J. Cohen et al, QUANTITATIVE MODEL FOR VENTRICULAR RESPONSE DURING ATRIAL FIBRILLATION, IEEE Transactions on Biomedical Engineering Volume 30, pages 769–782(1983)).

Ventricular instability is undesirable because it is uncomfortable for the patient and causes compromised hemodynamic parameters. Presently, symptomatic patients are treated with drugs which are frequently ineffectual and/or have undesirable side effects or they are treated with AV nodal ablation, a drastic procedure which causes the patient to become pacemaker dependent. However, stabilizing the ventricular rate during atrial fibrillation can lead to improved cardiac output, diastolic blood pressure, pulmonary artery pressure and end diastolic mitral valvular gradient. (C-P Lau, Leung, C-K Wong, Y-T Tai, C-H Cheng. A NEW PACING METHOD FOR RAPID REGULARIZATION OF RATE CONTROL IN ATRIAL FIBRILLATION, Am J Cardiol 65:1198–1203, (1990)).

It has been found that during atrial fibrillation, the ventricle can be stabilized at a rate approximately equal to the average intrinsic ventricular rate. Again, the mechanism of how the ventricle is stabilized by a pacing rate lower than the maximal intrinsic ventricular rate is not completely understood. It has been suggested that ventricular pacing eliminates or decreases the slope of the spontaneous depolarization phase of the AV node. F. H. M. Wittkampf, M. J. L. DeJongste, RATE STABILIZATION BY RIGHT VENTRICULAR PACING IN PATIENTS WITH ATRIAL FIBRILLATION. PACE 9:1147–1153 (1986). F. H. M. Wittkampf, M. J. L. DeJongste, H. I. Lie, F. L. Meigler. EFFECT OF RIGHT VENTRICULAR PACING ON VENTRICULAR RHYTHM DURING ATRIAL FIBRILLATION, J Am Coll Cardiol 11:539–545, (1988). These articles disclose that the ventricle may be stabilized by pacing approximately 95% of the ventricular depolarizations. However this method would cause ventricular pacing during atrial flutter and atrial fibrillation with a regular ventricular response which would not be beneficial and result in overpacing.

Another procedure (see Lau, supra) that was investigated to stabilize ventricular instability during atrial fibrillation was to apply an additional stimulus at a preselected interval after every sensed conducted ventricular beat. The average interval was about 230 ms. However it is believed that this procedure is unsatisfactory because it may result in pro-arrhythmia by pacing the ventricle during the vulnerable period of ventricular repolarization, and moreover, it is not an appropriate technique for arrhythmia classification.

The above-mentioned co-pending application Ser. No. 347,279 discloses an apparatus and method for stabilizing the ventricular rate by gradually increasing the pacing rate until stability is achieved. The apparatus and method also allow the pacing rate to decrease once stability is achieved to account for changing physiological conditions. The present disclosure pertains to an apparatus and method using a similar technique to interpret a relatively fast ventricular rhythm, i.e., to determine whether a cardiac arrhythmia is due to atrial fibrillation or some other tachycardia (i.e., ventricular, sinus, etc.).

In an article (Jenkins, J., Noh, K. H., Bump, T. et al. "A single atrial extra stimulus can distinguish sinus tachycardia from 1:1 paroxysmal tachycardia" Pace 9:1063–1068, 1986), an algorithm is described which made use of interactive pacing to classify arrhythmia. However this technique uses interactive atrial pacing, and therefore, would not be useful for atrial fibrillation treatment because of its inability to capture the atrium during atrial fibrillation. Moreover, this technique cannot be used to diagnose atrial fibrillation.

Other known techniques for cardiac arrhythmia classification include very accurate atrial rate and variability measurements, which require atrial sensing; atrial and/or ventricular morphology analysis, requiring complicated and sophisticated data processing analysis; analysis of the paced depolarization integral (PDI) in the atrium requiring atrial pacing and sensing electrode(s) and capture detection software. Even if available, atrial sensing for cardiac arrhythmia classification can be difficult because these signals often have a very low level and accordingly are hard to amplify and separate from noise, thereby confounding rate and morphology interpretation.

Another disadvantage of known techniques for atrial arrhythmia classification is that they all require an atrial sensing lead. However, the physician may not want to implant such a lead because it may be too difficult and time consuming, and/or the vein may be too small for such an atrial lead.

OBJECTIVES AND SUMMARY OF THE INVENTION

In view of the above, it is an objective of the present invention to provide a pacemaker which discriminates atrial fibrillation from ventricular tachycardia and/or supraventricular tachycardias so that proper therapy can be applied, if required.

A further objective is to provide a pacemaker, which, in case of atrial fibrillation, automatically decouples ventricular pacing from the atrium and provides electrical therapy to stabilize the ventricular rate.

Yet a further objective is to provide a single chamber pacemaker which can detect atrial fibrillation and provide automatic rate-stabilization therapy when atrial fibrillation is detected.

Another objective is to provide an apparatus and method for preventing the application of inappropriate atrial therapy.

Other objectives and advantages of the invention shall become apparent from the following description of the invention. Briefly, a pacemaker constructed in accordance with this invention includes a pace and sense circuit providing interfacing with the heart and a digital microprocessor receiving signals from the pace and sense circuit and providing, in response, control signals for cardiac pacing. Bradycardia applications of a ventricular rate stabilization algorithm were described in the above-named application Ser. No. 347,279. The present application is provided for discrimination of ventricular tachycardia (VT) and/or sinus tachycardia from atrial fibrillation.

Ventricular stability criteria to separate VT from AF have been described and implemented in anti-tachycardia pacemakers and ICDs. Previous method measure variability only. However, the ventricular rate during VT can be somewhat variable while during AF it can be somewhat consistent. The proposed method actively paces the ventricle during periods of ventricular instability, and if the ventricular rate is stabilized by the algorithm, AF would be detected or classified. If AF were detected (i.e., the rate was stabilized by the algorithm), the rate stabilizing algorithm can continue to function (if not at too high a rate) to improve the patient's condition. Alternately, atrial defibrillation may be applied, or the atrium and/or ventricle may be just monitored. Otherwise, if VT was detected, (i.e., the rate did not stabilize as a result of pacing) antitachycardia pacing or cardioversion would be effected. The present technique is designed to function between specific rate boundaries which correspond to hemodynamically stable arrhythmias for the particular patient. If the rate goes outside of these boundaries, other therapies or no therapy results. The apparatus and techniques disclosed herein may be implemented alone or in conjunction with a more comprehensive arrhythmia detection and management system.

DETAILED DESCRIPTION OF THE INVENTION

Figure 1:
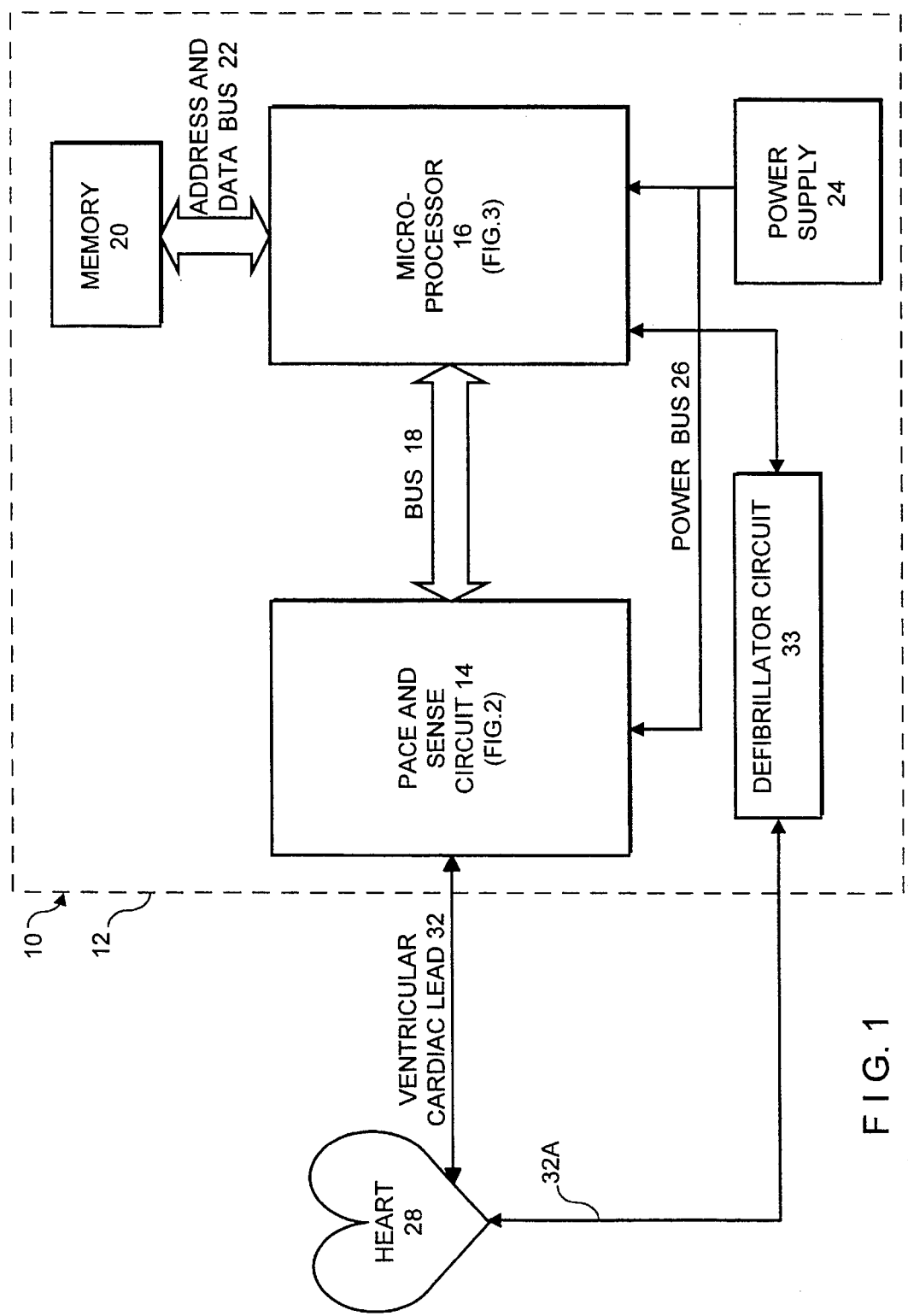
FIG. 1 shows a block diagram of a pacemaker constructed in accordance with this invention.

Referring now to FIG. 1, a pacemaker 10 constructed in accordance with this invention includes in the embodiment shown an implantable housing 12. The housing holds a pace and sense circuit 14, described in more detail in FIG. 2, and a microprocessor 16, described in more detail in FIG. 3. The pace and sense circuit 14 and the microprocessor 16 are interconnected by a bus 18 for exchanging data, as well as communication and control signals. The pacemaker 10 further includes a memory 20 connected to the microprocessor 16 by a data and address bus 22, and a power supply 24 providing power to the various components of pacemaker 10 via power bus 26.

Once implanted, the pacemaker 10 is connected to a patient's heart 28 by a lead 32 terminating in the right ventricular chamber. It should be understood that the arrangement of the pacemaker 10 and lead 32 do not form a part of this invention. Other arrangements may be used as well, using other types of leads including tri-polar leads, unipolar leads, one in each chamber and so on and the pacemaker may be operated in various modes. For example, in VDD mode lead 32 may be used as a "single-pass" lead, an arrangement which is well known in the art.

If the pacemaker 10 is an implantable defibrillator, then it also may include defibrillator electrodes such as 32A and defibrillator circuitry 33 for generating defibrillation pulses for the same.

Figure 2:
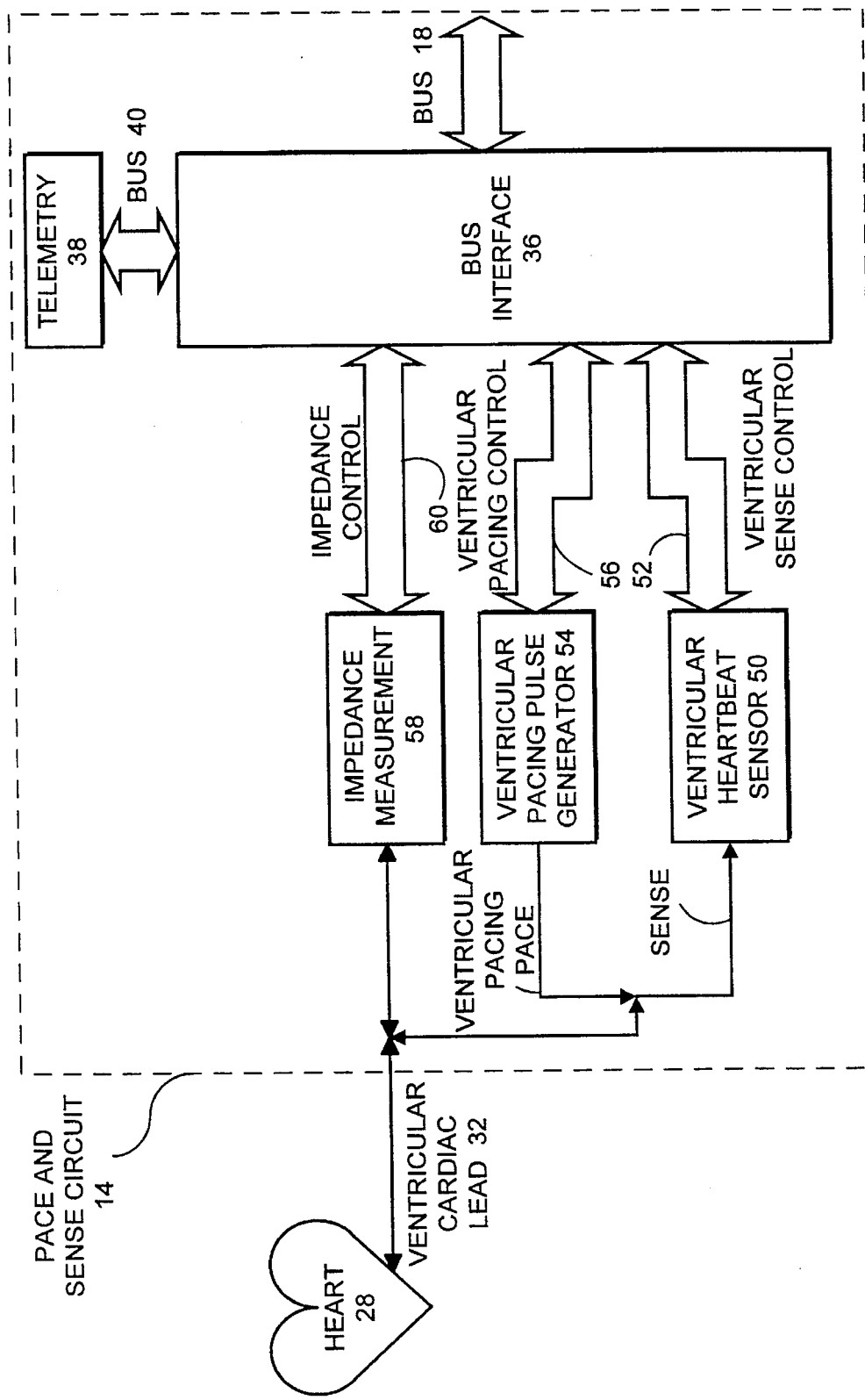
FIG. 2 shows a block diagram for the pace and sense circuit for the pacemaker of FIG. 1.

Referring now to FIG. 2, the pace and sense control circuit 14 includes a bus interface 36, a telemetry circuit 38 and various other sensing and control circuits for sensing the status of the chambers of heart 28 and to provide appropriate pacing signals thereto. The bus interface 36 provides interfacing with microprocessor 16 via bus 18. The telemetry circuit 38 provides communication with the outside world by, for example, inductive coupling. Signals with the telemetry circuit are exchanged via telemetering bus 40.

The ventricular chamber of heart 28 is sensed through ventricular cardiac lead 32 by ventricular heart-beat sensor 50, which is controlled by a ventricular sense control bus 52. Pacing pulses for the ventricular chamber are generated by the ventricular pacing pulse generator 54, controlled by the ventricular pacing control bus 56.

The impedance measurements are made through lead 32, by impedance measurement circuit 58 to determine the minute volume in a manner known in the art. This circuit is controlled by impedance control bus 60. All the control buses are interconnected between their respective circuits and the bus interface 36 to provide two way communication with the microprocessor 16.

Figure 3:
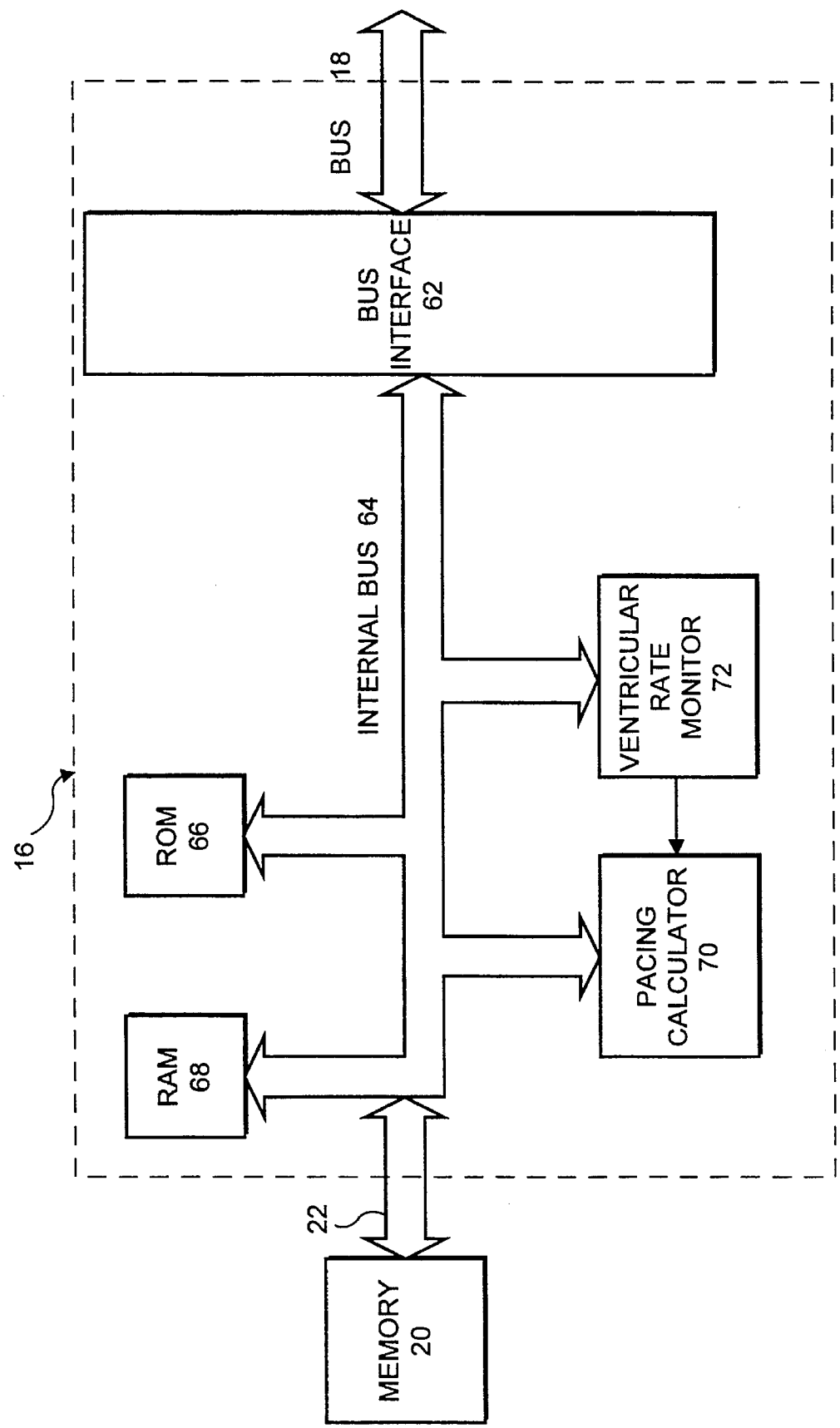
FIG. 3 shows a block diagram for the microprocessor of FIG. 1.

Referring now to FIG. 3, the microprocessor 16 includes a bus interface circuit 62 for interfacing with bus 18, and an internal bus 64 interconnecting the various components of the microprocessor 16. The microprocessor 16 further includes a read only memory (ROM) 66 used for storing programming information, a random access memory (RAM) 68 used as a scratch pad, a pacing calculator 70 and a ventricular rate monitor 72.

Briefly, impedance measurements using the lead 32 are made by impedance measurement circuit 58 at regular intervals. These sequential measurements are transmitted via control bus 60, bus 18 and internal bus 64 (through the interface circuits 36 and 62) to the pacing calculator 70. This calculator 70 converts these impedance measurements into a minute volume corresponding to the patient's metabolic oxygen demand and uses this parameter to calculate the ventricular pacing rate. Of course, any other rate responsive sensor could be used, including, for example, sensors based on body motion, temperature, right ventricular dp/dt, cardiac output, QT interval, paced depolarization integral, or combinations of these factors. Alternatively, no rate responsive sensor may be used at all.

The calculator 70 generates pacing control signals for pacing the heart in a particular mode. These control signals are transmitted to the pacing pulse generator 54 which in response generate appropriate pacing pulses to the ventricle as described above.

The ventricular heartbeat sense signals from sensor 50 are also fed to the ventricular rate monitor 72. This monitor uses the received signal to determine if the ventricular rate is stable. If the ventricular rate is unstable, the monitor requests the pacing calculator to change the ventricular pacing rate to a higher rate in an attempt to stabilize the ventricular rate. If the ventricular rate is successfully stabilized, atrial fibrillation is indicated and the monitor acts accordingly, as discussed below. Preferably calculator 70 and monitor 72 are implemented by software.

The operation of the microprocessor 16 for sensing and correcting cardiac arrhythmia shall now be described in conjunction with the flow chart of FIG. 4.

Initially, in step S100, the pacemaker monitors the intrinsic ventricular activity and provides bradycardia pacing. During the operation, the cardiac functions are monitored (S102) to detect cardiac arrhythmia (S104). If an arrhythmia is detected, this condition is classified (S106) using, for example, ventricular rate, or other criteria as described in Murphy Pat. No. 5,379,776 and others. If the arrhythmia is found to be a hemodynamically stable tachycardia (S108) then the procedure set forth below is followed. Otherwise, alternative classification and/or therapy is provided (S110).

More specifically, in step S112 the ventricle is paced at a rate, higher than the ventricular stand-by pacing rate. In step S114, in response to this pacing, the ventricular pacing rate is checked to determine if it has stabilized. If the ventricular rate is not stabilized, then alternate classification/therapy is provided in step S110 as discussed before. Otherwise, atrial fibrillation is suspected and confirmed in step S116. In step S118, the ventricular rate stabilization therapy is provided, or alternatively, the ventricle is paced at a lower rate.

Figure 4:
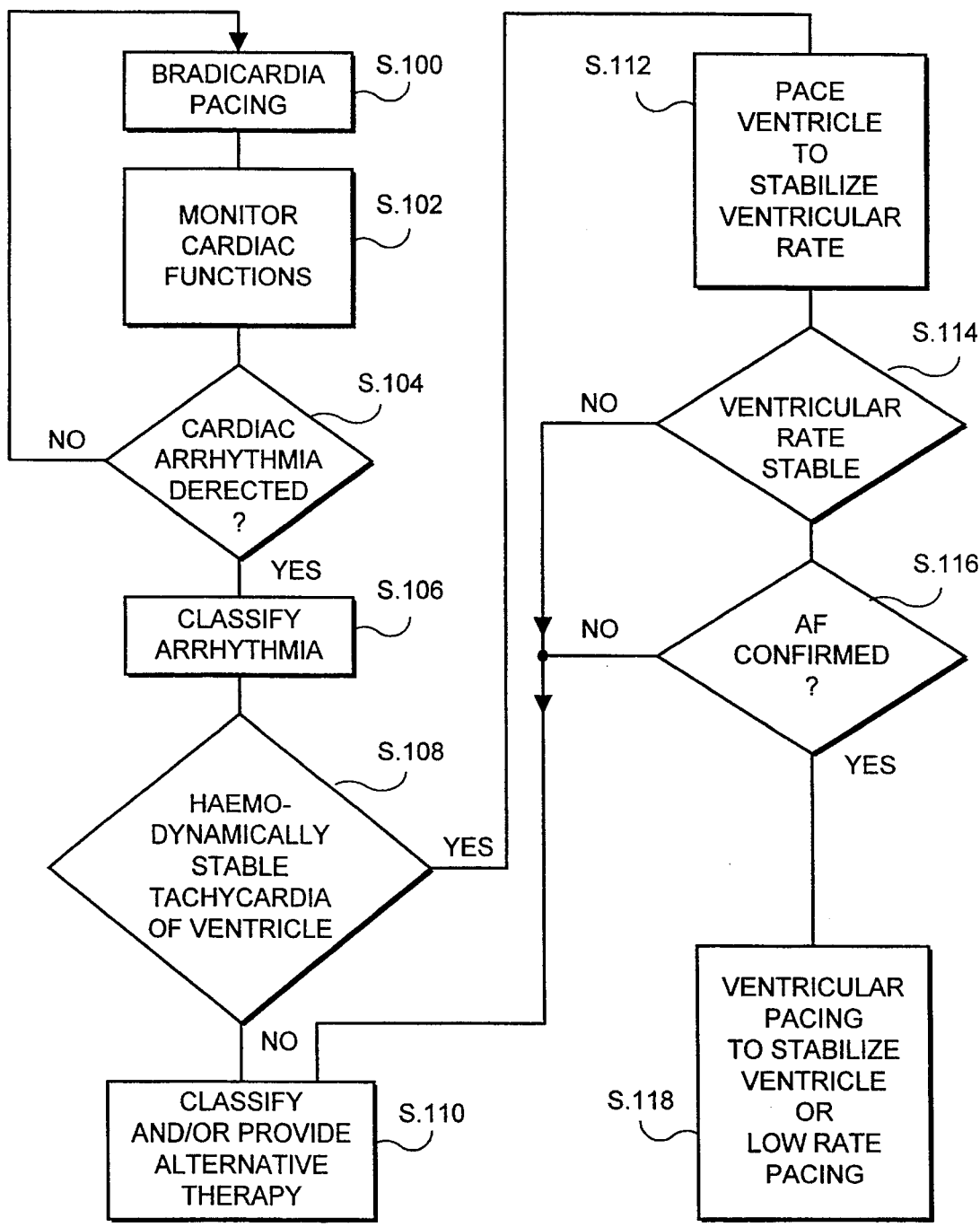
FIG. 4 shows a generalized flow chart for the microprocessor of FIG. 3.
Figure 5:
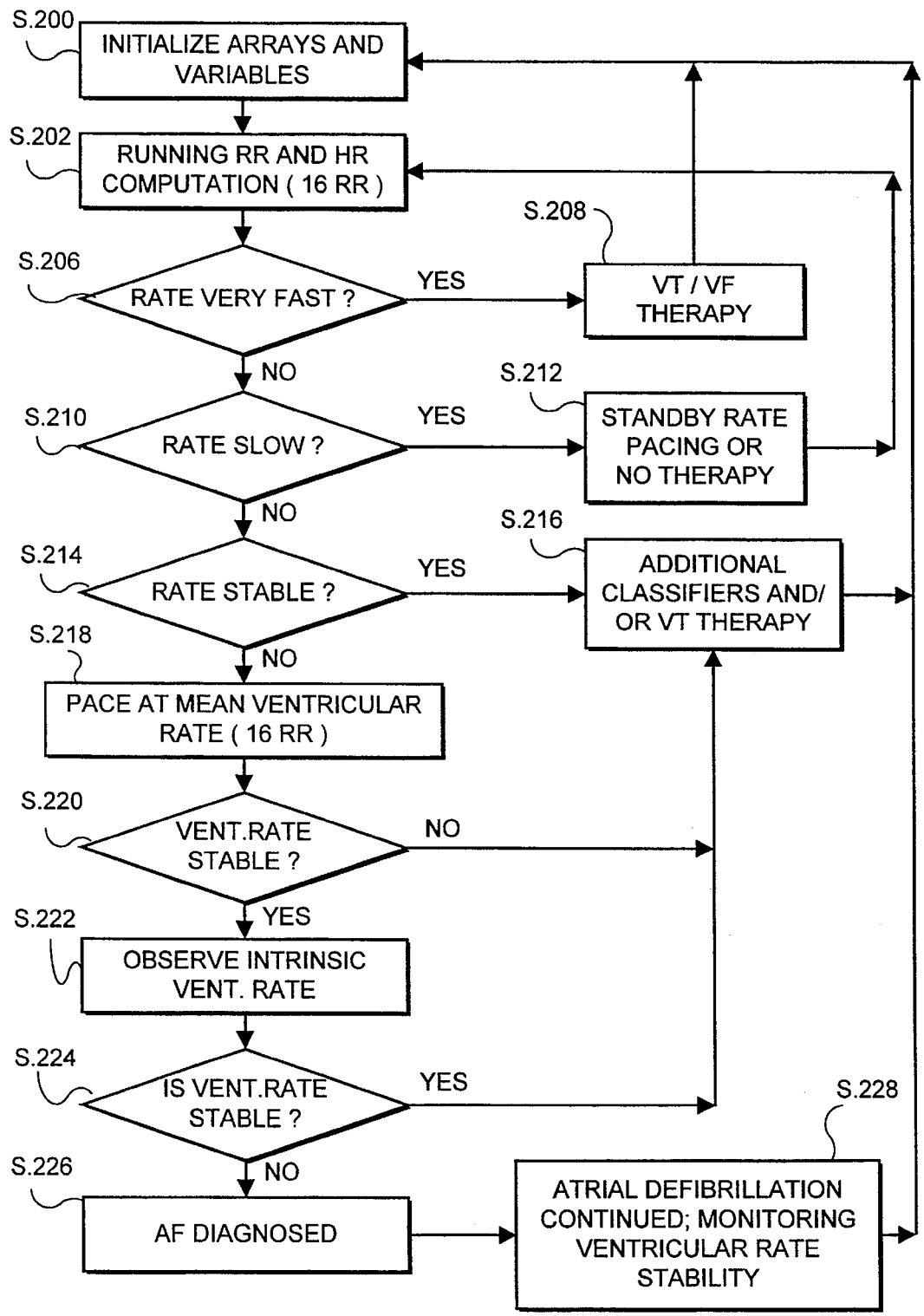
FIG. 5 shows a flow chart for a preferred embodiment of the invention.

A somewhat more detailed flow chart for a preferred embodiment of the invention is shown in FIG. 5. As part of monitoring the cardiac functions (step S102 in FIG. 4), in step S200 certain arrays and variables are initialized.

More specifically, as previously in step S202, the consecutive intrinsic ventricular pulses, i.e., the R-waves are sensed and the intervals RRi between the R-waves are measured. The heart rate HR for a predetermined number of intervals N is also determined. In a preferred embodiment of the invention N is 16.

In step S206, a determination is made as to whether the heart rate HR is fast (i.e., hemodynamically unstable). For example, if the heart rate HR is over 160 bpm (beats/minute), then alternate anti-tachycardia therapy is applied. This therapy may include ventricular antitachycardia pacing or ventricular defibrillation therapy, shown in step S208.

In step S210 a determination is made on whether the heart rate HR is below a certain threshold (such as 100 bpm). If the heart rate is below this threshold, then in step S212, bradycardia pacing, standby rate pacing or no therapy is applied.

In step S214 a determination is made as to whether the ventricular rate is stable, i.e., its variability is relatively low. If the ventricular rate is relatively stable then in step S216 additional classifiers may be used to define the cardiac arrhythmia and corresponding ventricular tachycardia (VT) therapy may be applied. Appropriate rhythms in S216 may be, for example, supra ventricular tachycardia, ventricular tachycardia, or atrial flutter.

If the ventricular rate is not stable as determined in S214 then in step S218 the ventricle is paced for N cycles at the mean ventricular rate of the previous N (e.g., 16) RR intervals (calculated in S202), in an attempt to stabilize it. Another statistical measure of HR or RR may be used, such as, median, a mean value plus ten beats/minute and so on. At the end of these intervals, in step S220, the ventricular rate over the previous N cycles is checked to determine if it was stabilized. If the ventricular rate was not stabilized then additional classifiers and other therapy may be applied in step S216 as discussed.

If in step S220 the ventricular rate was determined to be stabilized then in steps S222 and S224, the ventricle is paced at a low backup rate of about 50 ppm for the next 16 RR intervals. The purpose of these steps is to observe whether the intrinsic ventricular rate is unstable when the ventricular pacing rate is low (i.e., the ventricular pacing rate would not stabilize the ventricular rate). If the ventricle rate is now stable, then alternative therapy is applied, using for example, additional classifiers as discussed above (step S216).

Step S224 is provided as a means of confirming that the ventricular rate has not become stable since the onset of the tachycardia as determined earlier (see step S116 in FIG. 4). Optionally, steps S222 and S224 may be omitted.

If the intrinsic ventricular rate continues to be unstable, then atrial fibrillation is diagnosed in step S226. In response to this diagnosis, in step S228, therapy can be applied such as ventricular rate stabilization as described in the above mentioned application Ser. No. 347,279 or atrial defibrillation may be applied. Alternatively no therapy may be applied. In step S228, while ventricular pacing is applied, the ventricle is continuously monitored for ventricular tachyarrhythmias (e.g., ventricular rate and stability) to insure that this condition does not occur during the AF episode.

In summary, in FIG. 5, a three phase approach is disclosed, each phase lasting N RR intervals. N need not be the same for each phase. The first phase (steps 202–214) is used to determine if the heart rate is within a preselected range, and if so, whether the ventricular rate is stable. If the heart rate is outside the range, or if the ventricular rate is stable, alternate therapy is applied for ventricular fibrillation, tachycardia or bradycardia.

In the second phase (steps S218–220), an attempt is made to stabilize the ventricular rate. If the attempt is successful at the approximate mean ventricular rate then, in the third phase (steps S222–228) the intrinsic ventricular rate stability is observed for N cycles to confirm that the ventricular rate is due to atrial fibrillation. If the intrinsic ventricular rate has been verified as unstable, AF is diagnosed. Once AF is diagnosed, then atrial defibrillation therapy or ventricular rate stabilization (as described in Ser. No. 347,279) is applied or, optionally, no therapy is applied.

The stability of the ventricle required in steps S214, S220 or S224 can be established using a number of different methods. One method which is particularly advantageous is a so-called normalized mean absolute difference method described in detail below. This method is preferred because it is not very complex and hence can be easily implemented, and yet it has the ability to discriminate ventricular stability.

Briefly, as part of this method, the sequential RR intervals are first measured between adjacent R waves for N intervals as described above, and assigned sequential designations $RR_0, RR_1, RR_2, RR_3, \ldots RR_N$, the mean absolute difference parameter MADIFF is calculated using the formula:

$$MADIFF = \left[ \sum_{i=0}^{N-1} |RR_{(i+1)} - RR_i| \right] / \left[ \sum_{i=0}^{N-1} RR_i \right]$$

The numerator of this expression is obtained by taking the difference between adjacent $RR_1$ intervals and summing N of these differences. The denominator of this expression is obtained by adding N adjacent intervals $RR_1$. Dividing the sum of the differences by the sum of the intervals results in a parameter MADIFF, which is a normalized mean value for N intervals. This value MADIFF indicates the average variation of each interval from a given interval after N intervals have taken place.

For the purposes of the present invention, the parameter MADIFF is compared to a threshold level which may be for example 0.3 or 30%. A value of MADIFF above this threshold is indicative of an unstable and random ventricular activity.

A value below this threshold is indicative of a stable ventricular rate. The heart rate is related to $\Sigma RR_i$.

In the above-described embodiments, the control parameter used to make a determination about the stability of the ventricular rate is $RR_i$, defined as the interval between two adjacent R waves. Alternatively, the control parameter could be the interval between n R waves where n could be an integer greater than one. In other words, the control parameter is the time interval between two non-adjacent R waves. This alternative may be used to reduce the sensitivity of the apparatus to premature ventricular depolarizations.

During step S220, stability may also be measured by counting the number of ventricular senses.

FIGS. 4–5 and the description for these figures pertains to the preferred embodiments of the invention, and more particularly to a method and apparatus for confirming atrial fibrillation in association with a single chamber pacemaker.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable cardiac device for stimulating a heart, said pacemaker comprising:

means for monitoring a ventricle of said heart to sense ventricular rate instability; and means for pacing said ventricle;

wherein said means for monitoring detects atrial fibrillation based on a response of said ventricle to said ventricular pacing.

2. An implantable cardiac device comprising:

means for applying pacing signals to a ventricle in a patient's heart;

means for sensing intrinsic ventricular signals in the ventricle;

means for determining ventricular rate instability based on said ventricular signals;

means for controlling said pacing signals; and classifying means for classifying said ventricular instability as corresponding to one of atrial fibrillation and ventricular tachycardia from a response to said pacing signals.

3. A cardiac implant device comprising:

sensing means for sensing cardiac activity in a patient's heart;

pacing means for generating cardiac pacing pulses; and control means for controlling said pacing means in accordance with said cardiac activity, said control means including cardiac classifying means for classifying a cardiac condition of the patient's heart, said cardiac classifying means including means for monitoring a ventricle to sense a ventricular rate instability; said control means being provided to pace said ventricle at a rate selected to stabilize said ventricle, said classifying means classifying said cardiac condition as atrial fibrillation, if said pace stabilizes said ventricle.

4. The device of claim 3 wherein said classifying means further includes means for confirming said atrial fibrillation.

5. The device of claim 3 wherein said device further includes therapy application means for applying therapy after said atrial fibrillation condition has been identified.

6. A cardiac implant device comprising:

means for monitoring a ventricle to detect ventricular instability;

means for selectively pacing said ventricle to attempt to reduce said ventricular instability; and means for classifying a cardiac condition based on a response to said pacing, said means for classifying generating information indicative of atrial fibrillation if said ventricular instability is reduced by said pacing.

7. The device of claim 6 wherein said pacing is successful if said ventricular instability is reduced by a predetermined amount.

8. The device of claim 6 further comprising means for providing antitachycardia therapy to the patient's heart if said ventricular instability is not reduced by said pacing.

9. The device of claim 6 further comprising determining means for determining quantitatively said ventricular instability.

10. The device of claim 9 wherein each cardiac activity includes an R-wave, and said determining means includes means for measuring R-R intervals between successive R-waves.

11. The device of claim 10 wherein said determining means includes averaging means for taking an average of a plurality of R-R intervals.

12. The device of claim 6 further comprising confirming means for confirming atrial fibrillation after ventricular pacing by measuring a ventricular instability of the intrinsic ventricular rate.

13. An implantable cardiac device comprising:

means for applying pacing signals to a ventricle in a patient's heart;

means for sensing intrinsic ventricular signals in the ventricle;

means for determining ventricular rate instability based on said ventricular signals;

means for controlling said pacing signals; and classifying means for classifying said ventricular instability as corresponding to one of atrial fibrillation and supraventricular tachycardia from a response to said pacing signals.

14. A method of classifying the condition of a patient's heart comprising:

monitoring intrinsic cardiac pulses in a ventricle to provide a signal indicative of ventricular rate stability;

if the ventricular rate is unstable, attempting to stabilize said ventricular rate by pacing the ventricle at a test pacing rate;

if pacing at said test pacing rate stabilizes the ventricular rate, then classifying the condition of the heart as atrial fibrillation.

15. The method of claim 14 wherein said step of monitoring includes:

measuring intervals between a preselected number of successive intrinsic cardiac pulses;

determining a ventricular rate from said measurements; and comparing said ventricular rate to a preselected threshold.

16. The method of claim 15 after said comparing step further comprising the steps of:

determining if said ventricular rate is stable if said ventricular rate is within a preselected range;

if said ventricular rate is not stable, pacing said ventricle at said test pacing rate, said test pacing rate being related to said ventricular rate.

17. The method of claim 16 further comprising gradually reducing said test pacing rate until a preselected level is reached.

18. The method of claim 15 wherein said step of measuring intervals comprises measuring R-R intervals.

19. The method of claim 15 wherein said step of measuring intervals comprises monitoring successive R-R intervals and measuring excisions of each R-R interval from an average to determine a ventricular instability.

* * * * *

UNITED STATES PATENT AND TRADEMARK OFFICE
CERTIFICATE OF CORRECTION

PATENT NO. : 5,591,215

DATED : January 7, 1997

INVENTOR(S) : Saul E. Greenhut and Anthony Murphy

It is certified that error appears in the above-identified patent and that said Letters Patent is hereby corrected as shown below:

In the Abstract

Line 8     change "unsuccesful" to --succesful--.

Col. 7, line 21     change "$RR_i$" to --$RR_{\dot{i}}$--.

Col. 7, line 23     change "$RR_i$" to --$RR_{\dot{i}}$--.

Signed and Sealed this

Twenty-second Day of April, 1997

Attest:

BRUCE LEHMAN

Attesting Officer

*Commissioner of Patents and Trademarks*